(12) United States Patent  (10) Patent No.: US 8,150,524 B2
Maschino et al.  (45) Date of Patent: Apr. 3, 2012

(54) SELECTIVE NEUROSTIMULATION FOR TREATING EPILEPSY

(75) Inventors: Steven E. Maschino, Seabrook, TX (US); Stephen Brannan, Friendswood, TX (US)

(73) Assignee: Cyberonics, Inc., Houston, TX (US)

( * ) Notice: Subject to any disclaimer, the term of this patent is extended or adjusted under 35 U.S.C. 154(b) by 204 days.

(21) Appl. No.: 12/467,804

(22) Filed: May 18, 2009

(65) Prior Publication Data

US 2009/0234419 A1  Sep. 17, 2009

Related U.S. Application Data

(63) Continuation of application No. 11/261,182, filed on Oct. 28, 2005, now Pat. No. 7,555,344.

(51) Int. Cl.
 *A61N 1/18* (2006.01)
(52) U.S. Cl. ............................................ 607/45; 607/18
(58) Field of Classification Search .................. 607/45, 607/46, 115, 116, 118
See application file for complete search history.

(56) References Cited

U.S. PATENT DOCUMENTS

| 5,299,569 | A | * | 4/1994 | Wernicke et al. | 607/45 |
| 5,335,657 | A | * | 8/1994 | Terry et al. | 607/45 |
| 5,713,923 | A | * | 2/1998 | Ward et al. | 607/3 |
| 5,752,979 | A | * | 5/1998 | Benabid | 607/72 |
| 6,104,956 | A | * | 8/2000 | Naritoku et al. | 607/45 |
| 6,671,556 | B2 | * | 12/2003 | Osorio et al. | 607/45 |
| 6,788,975 | B1 | * | 9/2004 | Whitehurst et al. | 607/45 |
| 7,003,352 | B1 | * | 2/2006 | Whitehurst | 607/45 |
| 7,313,442 | B2 | * | 12/2007 | Velasco et al. | 607/45 |
| 7,499,752 | B2 | * | 3/2009 | Maschino et al. | 607/40 |
| 7,532,935 | B2 | * | 5/2009 | Maschino et al. | 607/45 |
| 7,801,601 | B2 | * | 9/2010 | Maschino et al. | 607/2 |
| 2003/0181955 | A1 | * | 9/2003 | Gielen et al. | 607/45 |
| 2006/0217781 | A1 | * | 9/2006 | John | 607/45 |
| 2006/0293721 | A1 | * | 12/2006 | Tarver et al. | 607/45 |
| 2008/0027503 | A1 | * | 1/2008 | Marrosu et al. | 607/45 |

* cited by examiner

*Primary Examiner* — Brian T Gedeon
(74) *Attorney, Agent, or Firm* — Timothy L. Scott; Darrell N. Fuller; Jonathan D. Rowell

(57) ABSTRACT

A method and device for treating epilepsy are disclosed which provide for electrical, chemical or magnetic stimulation of certain areas of the brain to modulate neuronal activity of areas associated with symptoms of epilepsy. Deep brain stimulation is combined with vagus nerve stimulation to enhance symptomatic relief of the disorder. Some embodiments also employ a sensing capability to optimize the therapeutic treatment regimen.

20 Claims, 4 Drawing Sheets

SELECTIVE NEUROSTIMULATION FOR TREATING EPILEPSY

CROSS-REFERENCE TO RELATED APPLICATIONS

This application is a continuation of U.S. patent application Ser. No. 11/261,182, now U.S. Pat. No. 7,555,344, filed Oct. 28, 2005. The entire content of this application is incorporated herein by reference.

BACKGROUND OF THE INVENTION

1. Field of the Invention

The present invention generally relates to methods and apparatus for stimulating certain areas of the brain to treat epilepsy by modulation of electrical activity of neural tissue in selected areas of the brain.

2. Description of Related Art

Epilepsy, or seizure disorder, is a chronic neurological condition characterized by recurrent seizures that begin in the brain and are associated with excessive or abnormal synchronization of neural activity. It has been estimated that about 1% of the population suffer from some form of epilepsy. The type of seizure experienced by an epilepsy sufferer during an epileptic event varies from one individual to another, but is usually one of the following types: absence seizures, partial seizures (petit mal), complex partial seizures, generalized tonic-clonic contractions of muscles (grand mal), temporal lobe seizures and generalized motor seizures. Partial onset seizures begin in a single part of the brain and remain localized to only that area (focal), while general onset seizures arise throughout the entire brain simultaneously (multi-foci). In some instances, a partial onset seizure can progress to involve much of the brain, in which case the seizure is said to be "secondarily generalized." Some seizures result in a loss of conscious awareness by the individual, and are termed "complex" seizures. Although consciousness is unimpaired in an individual suffering from "simple" seizures, that person may experience other symptoms such as sensory distortions, involuntary movements, and loss of muscle tone. The behavioral aspects of a seizure often reflect a function of the area or areas of the brain where the abnormal electrical activity takes place.

Neurologists recognize a number of distinct epilepsy syndromes which are usually classified according to the area or areas of the brain associated with the seizures. Among these are frontal lobe epilepsy, occipital lobe epilepsy, mesial temporal lobe epilepsy, parietal lobe epilepsy, benign myoclonic epilepsy in infants, juvenile myoclonic epilepsy, childhood absence epilepsy, juvenile absence epilepsy, epilepsy with generalized tonic clonic seizures in childhood, infantile spasms (West syndrome), Lennox-Gastaut syndrome, progressive myoclonus epilepsies, febrile fits, epilepsy with continuous spike and waves in slow wave sleep (ESES), Laudau Kleffner syndrome, and Rasmussen's syndrome.

The reasons why susceptible individuals develop epilepsy are not completely understood and there are many possible causes. Some epilepsy sufferers require treatment for many years to keep seizures under control. Treatment of epilepsy typically includes medication, and sometimes neurosurgical intervention (lesioning). U.S. Pat. No. 6,923,784 (Medtronic) describes drug infusion into the brain. Electrical stimulation of the vagus nerve using an implantable stimulator has proven successful in reducing the severity and/or frequency of seizures in some cases. U.S. Pat. No. 5,928,272 (Cyberonics, Inc.) describes such a device that is activated to generate a therapeutic waveform upon detecting a time rate of change in the patient's heart rate which is sufficiently abrupt and of sufficient magnitude to be inconsistent with normal physical activity, indicative of an imminent epileptic seizure. U.S. Pat. No. 6,920,357 (Osorio) describes certain vagal nerve stimulation techniques for treatment of epileptic seizures. U.S. Pat. No. 6,339,725 (Southern Illinois University) describes certain methods of modulating aspects of brain neural plasticity by vagus nerve stimulation. It is said that vagus nerve stimulation has been shown to cause activation of several parts of the brain that are specifically involved in cognitive processing, memory, learning, sensory and motor processing, and affects regions of the brain that are prone to developing epilepsy or which regulate the development of epilepsy. Studies have reportedly demonstrated that vagus nerve stimulation activates the amygdala and cingulate cortex, which are involved in learning and cognitive processing. Such stimulation also activates several thalamic nuclei which serve relay functions. In addition, it activates several sensory nuclei, including the auditory, visual, and somatic sensory systems. Finally, vagus nerve stimulation reportedly activates monoaminergic nuclei, especially the locus ceruleus and A5 groups, which provide norepinephrine to the brain. Another important site of activation is the dorsal raphe which provides serotonin to the brain.

There have also been reports of attempts to treat epilepsy by direct electrical stimulation of the brain (DBS). In DBS, neurons in the immediate vicinity of the electrodes are induced to fire (i.e., are recruited) by the electrical stimulus to modify the electrical activity in that area of the brain. U.S. Pat. No. 6,016,449 describes a brain stimulator implanted in the cranium and having leads terminating with electrodes in contact with brain tissue. U.S. Pat. No. 6,944,501 (Neurospace, Inc.) describes a neurostimulator that is configured to treat epilepsy and other neurological disorders using certain stimulation strategies including changing various pulse parameters, during the imposition of a burst of pulses. U.S. Patent Application Publication No. 2005/0021104 (DiLorenzo) describes a neurological control system for generating neural modulation signals delivered to a nervous system component through one or more intracranial stimulating electrodes in accordance with certain treatment parameters. Such treatment parameters may be derived from a neural response to previously delivered neural modulation signals sensed by sensors configured to sense a particular characteristic indicative of a neurological or psychiatric condition. U.S. Patent Application Publication No. 2005/0182453 (Advanced Bionics Corporation) states that because vagal nerve stimulation has been demonstrated to have anticonvulsant effects, it is said to be likely that changes in synaptic transmission in the nucleus of the solitary tract, a primary site at which vagal afferents terminate, can regulate seizure susceptibility. Certain drawbacks of available DBS implantable systems are described, and a method of treating epilepsy by implanting an electrical control unit within the patient to apply a stimulus including a current having a frequency of 400 Hertz or greater is described in U.S. Patent Application Publication No. 2005-0182453. It is said that the stimulus may additionally or alternatively include infusion of one or more drugs into the stimulation site. Stimulation sites in the brain are said to include seizure foci such as the thalamus (including centromedian, anterior, and ventrolateral nuclei and any other site of thalamic relay neurons), hippocampus, amygdala, cerebellum, nucleus tractus solitarius (NTS), locus coeruleus, and mesial temporal lobe. The stimulation site may also include any nerve branching from one of those sites, or an area of the brain that may propagate a seizure or that demonstrates increased activity in epileptics relative to non-epileptic controls.

Alternative ways to treat patients suffering from an epilepsy syndrome that is not sufficiently responsive to conventional therapies are needed.

SUMMARY OF THE INVENTION

Selective deep brain stimulation (DBS) together with vagus nerve stimulation will be beneficial for treating epilepsy when certain areas or regions of the brain are appropriately stimulated. Combined vagus nerve stimulation and DBS is expected to offer advantages over conventional therapies, and over vagus nerve stimulation or DBS alone. The preferred areas of the brain selected for treatment are those which are associated with symptoms of the particular seizure disorder to be treated. Bimodal treatment (e.g., electrical and chemical) is expected to be especially beneficial. Epilepsy syndromes for which treatment is contemplated include, but are not limited to, frontal lobe epilepsy, occipital lobe epilepsy, mesial temporal lobe epilepsy, parietal lobe epilepsy, benign myoclonic epilepsy in infants, juvenile myoclonic epilepsy, childhood absence epilepsy, juvenile absence epilepsy, epilepsy with generalized tonic clonic seizures in childhood, infantile spasms (West syndrome), Lennox-Gastaut syndrome, progressive myoclonus epilepsies, febrile fits, epilepsy with continuous spike and waves in slow wave sleep (ESES), Landau Kleffner syndrome, Rasmussen's syndrome, and congenital epilepsy due to inborn errors in metabolism. For ease of reference, the use of the term "epilepsy" herein includes, but is not limited to, the above-named syndrome types.

In accordance with certain embodiments of the present invention, a method of treating an individual suffering from epilepsy is provided. The method comprises (a) coupling a first stimulator to a stimulation site comprising a volume of neural tissue in an area of the individual's brain selected from the group consisting of insula, subcallosal area, cingulate, thalamus, prefrontal cerebral cortex, mesial temporal lobe, cerebellum, hypothalamus, hippocampus, amygdala, brain stem, occipital lobe, temporal lobe, frontal lobe, parietal lobe, Wernicke's area, area tempestas, basal ganglia, globus pallidus, superior colliculus, striatum, ventral striatum, ventral pallidum, caudate nucleus, putamen, nucleus accumbens, substantia nigra, ventral tegmentum, Brodmann areas 24, 25, 32, piriform cortex, ventricular region, ventral pallidum, and forebrain circumventricular organs, reticulate substantia innominata, rostral midbrain, red nucleus, periaqueductal gray, and white matter tracts leading to an aforementioned area or nucleus; (b) coupling a second stimulator to a site on the vagus nerve of the individual; (c) applying a first stimulation signal to the first stimulator such that the first stimulation signal causes modulation of the neuronal activity of neural tissue in the selected area of the brain; and (d) applying a second stimulation signal to the second stimulator such that the second stimulation signal causes modulation of the neuronal activity in the vagus nerve, wherein the combination of modulations attenuate at least one epilepsy symptom and/or deter recurrence of an epileptic event.

In step (d), the second stimulation signal causes stimulation of a site on the vagus nerve, whereby at least one vagus nerve pathway or neural activating circuit is affected causing a responsive effect on neural activity in at least one area of the brain to further attenuate the same or different at least one epilepsy symptom and/or to further deter recurrence of an epileptic event, in some embodiments of the method. In certain of those methods, the vagus nerve pathway is chosen from the group consisting of gustatory pathways, olfactory pathways, pro-inflammatory or anti-inflammatory pathways, respiratory pathways, cardiac pathways, baroreceptor pathways, somatosensory pathways, noradrenergic pathways, serotoninergic pathways, dopaminergic pathways, catecholaminergic pathways, GABAergic pathways, opioidergic pathways, cholinergic pathways, circuit of Papez, mesolimbic pathway, mesocortical pathway and nigrostriatal pathway. In some embodiments, the responsive effect on the area of the brain is excitatory or inhibitory and potentiates acute and/or long-term changes in neuronal activity of the area of the brain.

In certain embodiments of the above-described methods, the first and/or second stimulation signal causes modulation of neuronal activity in at least one brain area of the individual other than the area coupled to the first stimulator.

In certain embodiments of the above-described methods, the first stimulation signal comprises a first acute stimulation component and a first chronic stimulation component and/or the second stimulation signal comprises a second acute stimulation component and a second chronic stimulation component. In some of these embodiments, the first acute stimulation component comprises a higher intensity level of stimulation and shorter duration than the first chronic stimulation component and/or the second acute stimulation component comprises a higher intensity level of stimulation and shorter duration than the second chronic stimulation component.

In certain embodiments of the above-described methods, the first and/or second acute stimulation component comprises a duration in the range of one day to six months.

In certain embodiments of an above-described method of treating an individual suffering from epilepsy, the first stimulator is a first electrode and the second stimulator is a second electrode, and the method further includes (e) providing at least one programmable electrical signal generator coupled to the first and second electrodes; and (f) programming at least one electrical signal generator to define each of the first and second stimulation signals by a plurality of electrical parameters comprising a current magnitude, a pulse frequency, and a pulse width, wherein the parameters are selected to attenuate or deter the occurrence of at least one symptom of epilepsy.

In certain embodiments of an above-described method of treating an individual suffering from epilepsy, the first and/or second stimulator comprises at least one chemical dispensing assembly including a chemical-filled reservoir and a catheter in communication with a pump, the catheter comprising a dispensing end located on or near the nerve or brain area, and the first and/or second stimulation signal each comprises a therapeutic pumping signal. In these embodiments, the method comprises (c') operating at least one said pump such that the chemical contacts the vagus nerve and/or the brain area, whereby the neuronal activity of the contacted nerve and/or brain area is modified, and such modification of neuronal activity causes attenuation or deterrence of at least one symptom of epilepsy. The chemical agent may comprise one or more inhibitory neurotransmitter agonists, excitatory neurotransmitter antagonists, agents that increase the level of an inhibitory neurotransmitter, agents that decrease the level of an excitatory neurotransmitter, and local anesthetic agents, for example. In certain of these embodiments, the area of the individual's brain that is stimulated comprises the thalamus or a white matter tract leading to a portion of the thalamus. Alternatively, another of the above-mentioned areas, or white matter tracts leading to such areas, may serve as the chemical stimulus site in the brain.

In accordance with still another embodiment of the present invention, a method of treating an individual suffering from epilepsy is provided which comprises (a) providing a controller comprising a signal generator and processor in communication with a first electrode and a second electrode; (b) coupling the first electrode to a site on the vagus nerve of the individual; (c) coupling the second electrode to a volume of neural tissue in an area of the individual's brain selected from the group consisting of insula, subcallosal area, cingulate, thalamus, prefrontal cerebral cortex, mesial temporal lobe, cerebellum, hypothalamus, hippocampus, amygdala, brain stem, occipital lobe, temporal lobe, frontal lobe, parietal lobe, Wernicke's area, area tempestas, basal ganglia, globus pallidus, superior colliculus, striatum, ventral striatum, ventral pallidum, caudate nucleus, putamen, nucleus accumbens, substantia nigra, ventral tegmentum, Brodmann areas 24, 25, 32, piriform cortex, ventricular region, ventral pallidum, and forebrain circumventricular organs, reticulate substantia innominata, rostral midbrain, red nucleus, periaqueductal gray, and white matter tracts leading from an aforementioned area or nucleus; (d) applying a predetermined electrical signal to the first electrode, to modulate the vagus nerve; (e) sensing electrical activity in the selected volume of brain tissue by the second electrode; (f) comparing the resulting sensed electrical activity to a predetermined electrical state of the selected area; and (g) determining from the comparison whether the application of the predetermined electrical signal to the first electrode causes a modulation of electrical activity of the brain area, wherein the modulation of electrical activity corresponds to attenuate, or deter the occurrence of, at least one symptom of epilepsy. In certain embodiments, this method further comprises (h) adjusting the predetermined signal according to the comparison results, to alter the modulation of neuronal activity in the selected brain area to further attenuate, or deter the occurrence of, at least one symptom of epilepsy.

In certain embodiments of the above-described methods, the selected portion of the cingulate comprises the cingulate gyrus comprising the anterior cingulate or the posterior cingulate; the selected portion of the cortex comprises the motor cortex, prefrontal cortex, orbitofrontal cortex, premotor cortex, somatosensory cortex, cingulate cortex, anterior cingulate cortex, insular cortical region or any of Brodmann areas 8, 9, 10, 11; the selected portion of the thalamus is the ventral medial thalamic nucleus, ventral posterior medial thalamic nucleus, parafascicular nucleus, subthalamic nucleus, dorsomedial thalamic nucleus, intralaminar thalamic nuclei, midline thalamic nuclei, anterior thalamus, anterior thalamic nuclei, nucleus reticularis thalami, or centromedian nucleus of the thalamus; the selected portion of the hypothalamus is the lateral hypothalamus, paraventricular nucleus of the hypothalamus, the bed nucleus of the stria terminalis, mamillary bodies, supraoptic nucleus, dorsomedial nucleus of the hypothalamus, lateral nucleus of the hypothalamus, or tuberal nucleus of the hypothalamus; and the selected portion of the brainstem/medulla is the locus ceruleus, dorsal raphe nucleus, nucleus of the solitary tract, the entirety of the solitary tract, the caudal ventrolateral medulla, rostral ventrolateral medulla or parabrachial nucleus.

Further provided in accordance with certain embodiments of the present invention is an adaptive brain stimulation process for treating a patient suffering from an epilepsy syndrome, which comprises: (a) providing a system comprising at least one sensor for coupling with a status indicator site on the patient to sense a present state of at least a first brain region or set of brain regions; a first stimulating circuit for coupling at least the first brain region or set of brain regions by at least one stimulation electrode, to carry out stimulation according to a first set of stimulation parameters; a comparator adapted for coupling with at least one sensor, the comparator adapted for receiving data related to the present state and comparing the present state data with reference state data, such that the comparing results in a positive outcome or a negative outcome; and at least one control circuit coupled with at least the first stimulating circuit and adapted for being adjusted according to the outcome of the comparing of the present and reference states, to control the stimulation parameters; (b) stimulating at least a first brain region or a first set of brain regions of the patient according to a first set of stimulation parameters; (c) stimulating at least one site on the vagus nerve of the patient according to a second set of stimulation parameters; (d) sensing a present state of the patient to provide sensed data; (e) comparing the sensed data with reference state data to derive comparison results; (f) determining from the comparison results whether a change in the stimulation parameters is necessary for treating the patient's epilepsy syndrome; (g) if a change is determined to be necessary, determining what changes are to be made in the stimulation parameters; (h) changing the first set of stimulation parameters as determined in step (f); and (i) repeating steps (e)-(h) with the resulting changed stimulation parameters, until no further change is determined to be necessary in step (f). In certain embodiments, step (d) comprises sensing a state of one or more peripheral regions of the patient's body. In certain embodiments, changing the stimulation parameters in step (h) comprises adjusting parameters of the stimulation signal to stimulate a site on the vagus nerve to activate at least one vagus nerve pathway or neural activating circuit chosen from the group consisting of the gustatory pathways, olfactory pathways, pro-inflammatory or anti-inflammatory pathways, respiratory pathways, cardiac pathways, baroreceptor pathways, somatosensory pathways, noradrenergic pathways, serotoninergic pathways, dopaminergic pathways, catecholaminergic pathways, GABAergic pathways, opioidergic pathways, cholinergic pathways, circuit of Papez, mesolimbic pathway, mesocortical pathway and nigrostriatal pathway.

Still further provided in accordance with certain embodiments of the present invention is an adaptive brain stimulation system comprising: (a) at least one first biological sensor for coupling with a first brain region, or first set of brain regions, to sense the present state of at least one biological parameter of the first region or set of regions; (b) at least one second biological sensor for coupling with a neural tissue or set of neural tissues, other than said first brain region or first set of brain regions, to sense the present state of at least one biological parameter of said neural tissue or set of neural tissues, in said patient. In preferred embodiments, the neural tissue comprises at least one site on the vagus nerve. The method further comprises: (c) a first stimulating circuit comprising a first stimulation electrode for coupling with the first brain region or set of brain regions of the patient, to stimulate the first region or set of regions according to a first set of stimulation parameters; (d) a second stimulating circuit comprising a second stimulation electrode for coupling with said neural tissue or set of neural tissues, to stimulate said neural tissue or set of neural tissues according to a second set of stimulation parameters; (e) a comparator coupled with the first and second sensors to receive data related to the present states and compare a present set data with a reference state data, the comparing leading to a positive outcome or a negative outcome; and (f) control circuits coupled with the comparator and with the first and second stimulating circuits, for controlling the first and second set of stimulation parameters according to the outcome of the comparing of the present and reference states.

These and other embodiments, features and advantages will be apparent from the following detailed description and drawings.

DETAILED DESCRIPTION OF THE PREFERRED EMBODIMENTS

Definitions

Figure 1:
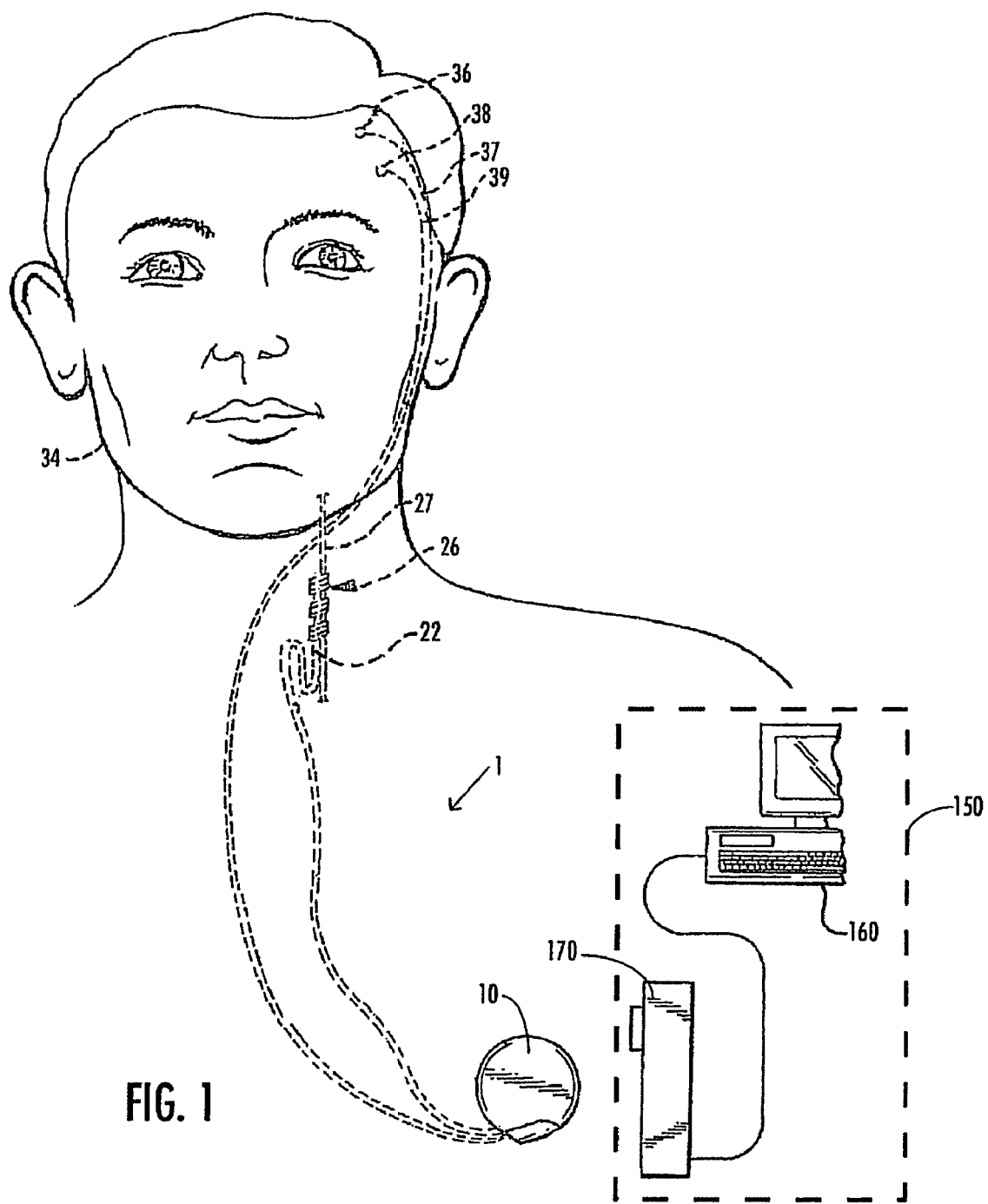
FIG. 1 is a simplified illustration of an electrode and neurostimulator placement configuration for treating epilepsy in accordance with an embodiment of the present invention.

The term "epilepsy" refers to any of a variety of types of epilepsy syndromes, including, but not limited to, frontal lobe epilepsy, occipital lobe epilepsy, mesial temporal lobe epilepsy, parietal lobe epilepsy, benign myoclonic epilepsy in infants, juvenile myoclonic epilepsy, childhood absence epilepsy, juvenile absence epilepsy, epilepsy with generalized tonic clonic seizures in childhood, infantile spasms (West syndrome), Lennox-Gastaut syndrome, progressive myoclonus epilepsies, febrile fits, epilepsy with continuous spike and waves in slow wave sleep (ESES), Laudau Kleffner syndrome, Rasmussen's syndrome, and epilepsy arising from an inborn error in metabolism.

While epilepsy is a type of neurological disorder, the term "neurological disorder" as used herein also refers to motor disorder such as tremor and the class of tremor disorders, intentional tremor, dystonia, tardive-diskenesia, ballism, spasticity, athetosis, rigidity, akinesia, bradykinesia, or other hyperkinetic or hypokinetic disorder, coma and paralysis.

As used herein, the terms "stimulating" and "stimulator" generally refer to delivery of a signal, stimulus, or impulse to neural tissue for affecting neuronal activity of a neural tissue (e.g., a volume of neural tissue in the brain or a nerve). The effect of such stimulation on neuronal activity is termed "modulation"; however, for simplicity, the terms "stimulating" and "modulating," and variants thereof, are sometimes used interchangeably herein. The effect of delivery of the signal to the neural tissue may be excitatory or inhibitory and may potentiate acute and/or long-term changes in neuronal activity. For example, the effect of "stimulating" or "modulating" a neural tissue may comprise one or more of the following effects: (a) changes in neural tissue to initiate an action potential (bi-directional or uni-directional), (b) inhibition of conduction of action potentials (endogenous or externally stimulated) or blocking the conduction of action potentials (hyperpolarizing or collision blocking), (c) affecting changes in neurotransmitter/neuromodulator release or uptake, and (d) changes in neuro-plasticity or neurogenesis of brain tissue. Applying an electrical signal to neural tissue may comprise generating a response selected from the group consisting of an afferent action potential, an efferent action potential, an afferent hyperpolarization, an efferent hyperpolarization, an afferent sub-threshold depolarization, and an efferent sub-threshold depolarization.

"Deep brain stimulation" (DBS) refers to direct or indirect application of a stimulus to an area within the brain. Such stimulation may be electrical, chemical (e.g., drug or pharmaceutical), or magnetic and may be applied directly or indirectly to the neural tissue of the brain. Similarly, deep brain sensing refers to the detection of an electrical or chemical signal from within the brain.

Vagus nerve stimulation is sometimes referred to herein simply as "VNS".

The terms "couple," "couples," "coupled," and "coupling" refer to either indirect or direct electrical connection, or placement of a chemical catheter outlet.

"Predetermined electrical signal" or "therapeutic electrical signal" refers to an electrical pulse, or pattern of electrical pulses, having defined parameters such as pulse current, pulse width, frequency, on-time and off-time.

"Chemical stimulation" and "chemical agent" refer to either chemical, drug or pharmaceutical agents capable of stimulating neuronal activity in a nerve or in neural tissue exposed to such agent. Examples of such agents are inhibitory neurotransmitter agonists, excitatory neurotransmitter antagonists, agents that increase the level of an inhibitory neurotransmitter, agents that decrease the level of an excitatory neurotransmitter, and local anesthetic agents.

Description

Various embodiments of the invention focus on certain areas of the brain that have not been previously correlated with causation or alleviation of epilepsy or other seizure disorders. Those areas are believed to comprise nodes in the neural circuitry that relate to the manifestation of epilepsy, and may be modulated to affect the occurrence, frequency and/or severity of epileptic seizures in an individual. It is proposed that the combination of vagus nerve stimulation and brain stimulation is useful for optimizing brain stimulation signal parameters, and that the therapeutic combination of VNS and DBS provides an effective treatment strategy for patients suffering from epilepsy.

Target sites of particular interest for brain stimulation and/or sensing include, but are not limited to, insula, subcallosal area, cingulate, thalamus, prefrontal cerebral cortex, brain stem, cerebellum, and white matter tracts leading to an aforementioned area, centromedian fascicular complex, ventral medial (Vim) thalamic nucleus, ventral posterior medial nucleus (VPM), parafascicular complex, other portion of the thalamus, entirety of the thalamus, subthalamic nucleus (STN), caudate, putamen, cingulate gyrus, nucleus locus ceruleus, the fronto-basal ganglionic-thalamocortical system and white matter tracts leading thereto, motor cortex, premotor cortex, somatosensory cortex, other sensory cortical regions, Wernickie's area, ventricular region, paraventricular region, ventral striatum, the ventral Pallidum anterior nucleus of the thalamus, dorsomedial nucleus of the thalamus, intralaminar thalamic nuclei, the cingulate cortex, hippocampus, mamillary bodies, the lateral hypothalamus, the locus ceruleus, the dorsal raphe nucleus, nucleus of the solitary tract (NTS), the caudal ventrolateral medulla (CVL), and rostral ventrolateral medulla (RVL), paraventricular nucleus of the hypothalamus, the bed nucleus of the stria terminalis, the prefrontal cortex, orbitofrontal cortex, the supraoptic nucleus, and forebrain circumventricular organs, ventral tegmentum, the Substantia Nigra Pars Compacta and reticulate ventral medial nucleus (VMb) parabrachial nucleus (PBN), midline thalamic, hypothalamic, amygdala, basal ganglia, the subthalamic nucleus, substantia nigra, pallidal, cerebellum, motor cortex, hypothalamus, substantia innominata, n. accumbens, anterior cingulate cortex, the insular cortical region, and area tempestas. It is also proposed that sensing of neuronal activity may be beneficially employed in conjunction with modulation of one or more of those areas of the brain to adapt or modify stimulation parameters of a neurostimulation system and to optimize or enhance a therapeutic treatment regimen for treating an individual patient's epilepsy syndrome.

Deep Brain Stimulation (DBS) System for Treatment of Epilepsy.

Referring to FIG. 1, a neurostimulator system 1 is shown as configured for treating epilepsy in a patient 34 by modulating the electrical activity of selected areas of the brain that are associated with symptoms of the disorder. System 1 generally includes at least one implantable stimulator device (stimulator) 36, preferably an electrode, in communication with a microprocessor-based control device (controller) 10. Alternatively, the stimulator (electrode) can be external to the patient, for being controlled and operated remotely through telemetry.

Figure 2:
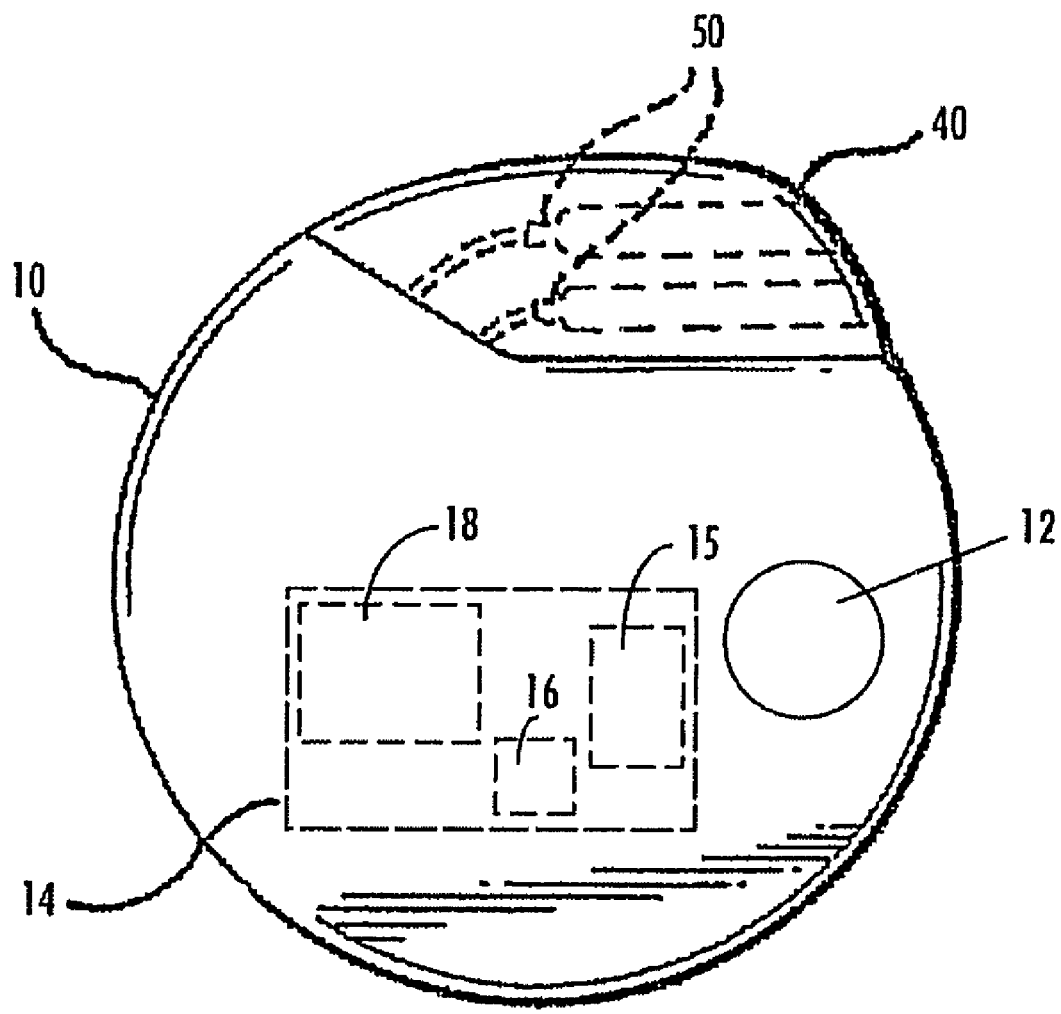
FIG. 2 is a fragmentary illustration of a controller containing a battery and programmable electronics package (shown as a block diagram), for use in treating epilepsy in accordance with an embodiment of the present invention.

Stimulator. For ease of reference, the stimulator or stimulus applicator is sometimes referred to herein as simply "the electrode." It should be understood, however, that stimulation of a nerve or neural tissue can be electrically, chemically or magnetically mediated, or a combination of any or all of those modes. An electrode is designed for placing in direct contact with a volume of neural brain tissue to be stimulated and/or sensed, as may be required. Alternatively, at least one electrode is selected which is suitable for placement in proximity to the target neural tissue. For electrical stimulation mode, the controller 10 is coupled to each electrode 36 by transcranial lead(s) 37, and is designed for applying an electrical signal to the selected area using the electrical signal generator unit 15 of controller 10 (FIG. 2). Lead(s) 37, 39 attach to the controller 10 at connectors 50 of header 40. Electrode/lead assemblies of this type are commercially available from known suppliers. Alternatively, lead(s) 37 is/are omitted and at least one implanted electrode comprises an induction receiver and controller 10 is configured to remotely modulate the target neural tissue through telemetry via an external transmitter. A suitable electrode of this type is commercially available from known suppliers.

Sensor. The system may also include at least one implantable sensing electrode (sensor) 38. The sensor is designed to measure endogenous neural activity or activity induced by modulation through actions of the controller 10 and is in communication with the control device 10 via lead(s) 39. Accordingly, the system may be adapted for applying the stimulation signal in response to a preselected triggering event (such as a seizure), from sensed physiological activity, from an external actuator, from brain imaging data, or from physician or patient input, as discussed in more detail below. The sensed parameter may be endogenous neural activity or activity induced by modulation through actions of a control device. Suitable sensing electrodes and other sensing devices capable of sensing physiological parameters are commercially available from known sources. U.S. Pat. No. 5,304,206 discloses a patient-activated implantable stimulator, and U.S. Pat. No. 5,928,272 describes an auto-activated neurostimulator adapted to sense a heart rate change indicative of an imminent epileptic seizure. The disclosures of those patents are hereby incorporated herein by reference.

Controller. Certain parameters of the stimuli generated by the controller 10 are programmable. System 1 comprises an internal or external system capable of measuring, sensing, recording, monitoring the physiological activity, physiological event, physiological threshold, body or brain state. Additionally, the system may be designed to vary the treatment parameters, based on adaptive learning whereby the device senses activity or physiologic changes after stimulation (electrical, chemical/pharmaceutical, magnetic) and automatically adjusts the controller to attempt to deliver optimized therapy. In that case, the controller 10 can also sense the result of adverse stimulation and adjust the stimulation to prevent an adverse patient response.

As shown in FIG. 1, an external programming system 150 is employed for implantable electrical medical devices. External programming system 150 is preferably capable of wireless (e.g., radio frequency) communication with the controller 10, and comprises a computer 160 and a wand 170 having an RF transmitter and receiver. Computer 160 may comprise a handheld computer operable by a healthcare provider. Wand 170 is capable of communicating with a receiver and transmitter in controller 10, and may be used to receive data from or transmit data to the controller 10.

FIG. 2 illustrates a preferred embodiment of the implantable control device 10 which comprises a programmable electronics package 14 containing a signal generator 15, a monitoring unit (monitor) 16 for transmitting control signals to/from the implanted electrode(s) and sensor(s), as appropriate, and a processing unit (processor) 18 for recording, measuring, sensing or monitoring physiologic data and comparing it to stored values, baseline values, reference or expected values and performing calculations on best treatment parameters. A power source 12 is also contained in controller 10. The programmable processor is configured to adjust and transmit stimulus parameters to the stimulator assembly in order to treat the disorder. The monitoring data can be stored digitally for future processing or diagnosis. A generally suitable form of implantable controller/pulse generator for use in the system and method of the present invention is disclosed, for example, in U.S. Pat. No. 5,154,172, assigned to the same assignee as the instant application (the device also referred to as a NeuroCybernetic Prosthesis or NCP device (NCP is a trademark of Cyberonics, Inc. of Houston, Tex., U.S.A.)

Figure 3:
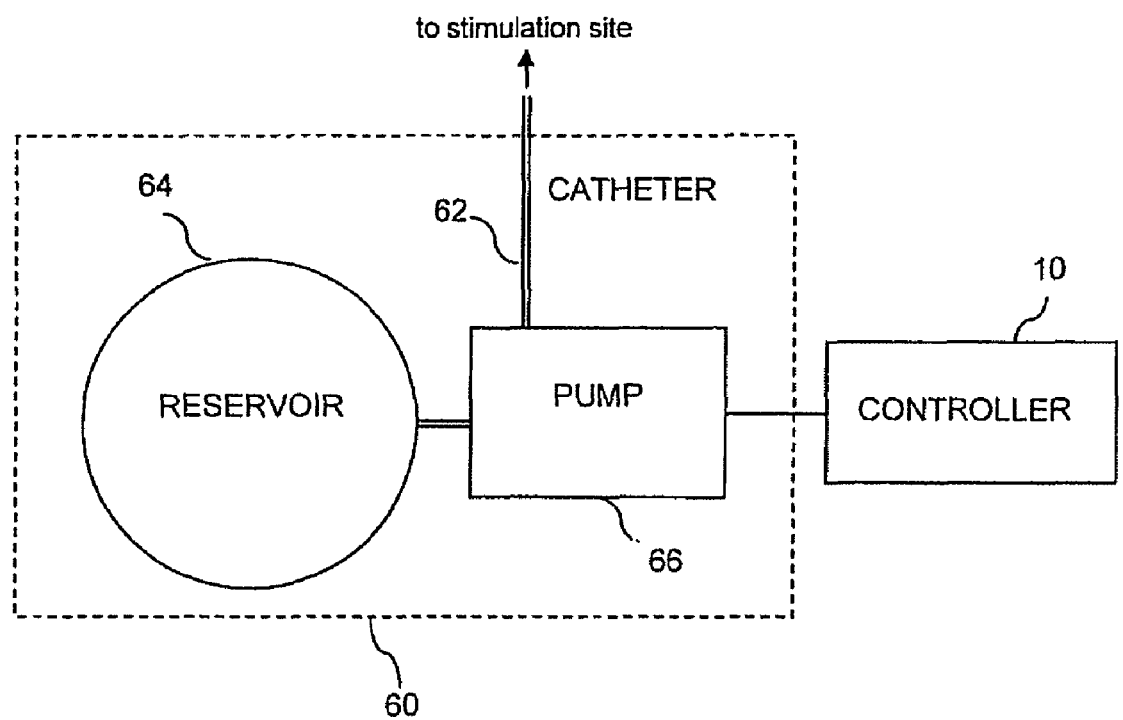
FIG. 3 is a schematic block diagram showing a chemical stimulation assembly according to an embodiment of the present invention.

Electrical, chemical, magnetic stimulation. Although the use of one or more electrodes as the stimulus application device (stimulator) for delivering electrical stimulation to the target neural tissue is preferred, it is also contemplated that the neurostimulator system could instead, or additionally, include a chemical or pharmaceutical applicator for applying a therapeutic stimulus to the target neural tissue effective to modulate the activity of the neural tissue to ameliorate the seizure disorder. The chemical stimulus application device 60 may comprise a chemical-filled reservoir 64 in fluid communication with a catheter 62 and pump 66 that is either implantable or has both implantable (catheter) and external (pump) components, or another suitable chemical delivery device could be included in the system (FIG. 3). The pump is coupled to controller 10. Examples of the types of chemicals or drugs that may be beneficially employed are inhibitory neurotransmitter agonists or antagonists, excitatory neurotransmitter agonists or antagonists, chemicals that increases the level of an inhibitory neurotransmitter, chemicals that decrease the level of an excitatory neurotransmitter, and local anesthetics. Control signals may be transmitted to or from either an electrode on the nerve, electrode or sensor in the brain, from a chemical delivery device and/or sensor, or from an internal or external monitoring unit via telemetry and/or through signals transmitted through conductive leads, as provided in the programmable circuitry.

In another configuration of the neurostimulation system, the stimulator is omitted and the system is designed for noninvasively applying a magnetic stimulus to a selected nerve or neural tissue from an external source via a transcranial magnetic stimulator (not shown), as are known in this field. Accordingly, it should be appreciated that neural tissue modulation can be electrically, magnetically or chemically/pharmaceutically mediated.

Still another configuration of the neurostimulation system substitutes an electrode designed for dural or subdural placement adjacent an area of the brain such as the orbitofrontal cortex area, instead of using an electrode for deep brain implantation. Dural or subdural electrodes may be designed for applying electrical stimulation or for sensing electrical activity, or both.

In still another configuration of the system, also shown in FIG. 1, the neurostimulation system includes at least one stimulator and/or sensor 26 for coupling directly or indirectly to at least one area or branch of the vagus nerve 27. Sensor 26 is coupled to controlled 10 by lead 22. Alternatively, electrodes suitable for placement on, or proximal to, the left and/or right vagus nerve(s) in a near-diaphragmatic location (e.g., supra-diaphragmatic or sub-diaphragmatic) may be included in the system. These may be stimulating and/or sensing electrodes.

Another embodiment of the system is an adaptive brain stimulation system that includes one or more biological sensors coupled to a patient for sensing a present state of at least a first brain region or a first set of brain regions. In this embodiment, the programmable electronics package 14 includes at least one stimulating circuit coupled with at least the first brain region or first set of brain regions of the patient by at least one electrode to carry out stimulation according to a set of stimulation parameters. The electronics package includes a comparator coupled with one or more above-described biological sensors to receive data related to the present state of the first brain region, or first set of brain regions, to provide a set of present state data. The comparator is also programmed to compare the set of present state data to reference state data, to determine a positive outcome or a negative outcome as to a present state of the first brain region or set of regions. For example, a positive outcome might be a beneficial cessation of abnormal synchronous electrical activity in a first brain region of a person suffering from epilepsy, in response to application of a stimulus to the person's brain. Similarly, a negative outcome might be a determination that there was no alleviation of such abnormal synchronous electrical activity in response to a stimulus. In an adaptive system, the programmable electronics package provides one or more control circuits coupled, with one or more stimulating circuit, that are able to be adjusted according to the outcome of comparing the present and reference states, to control the set of stimulation parameters.

Programmable control. The control device is designed so that control signals are transmitted from an internal or external monitoring unit to the electrode(s) and/or sensor(s). The neurostimulation system 1 is preferably capable of delivering to the target neural tissue a stimulatory electrical signal that can be intermittent, periodic, random, paired-pulses, coded or patterned. Stimulation frequency can be 0.1 to 2500 Hz, pulse width 1-2000 micro seconds, current amplitude 0.1 mA to 10 mA. Stimulation can be applied via either a cathode (−) electrode or anode (+) electrode. In some embodiments, the stimulating circuit(s) provide direct stimulation, and in other embodiments stimulation is provided by induction.

Manual activation/deactivation. The system design may be varied to provide a manual activation or deactivation switch in association with controller 10. Similar devices for manual and automatic activation of implantable medical devices are known, such as are disclosed in U.S. Pat. No. 5,304,206 (Cyberonics, Inc.). For example, manual activation or deactivation of the signal generator is achieved using a device such as an accelerometer or a piezoelectric element mounted to the inner surface of the controller housing so as to detect light taps by the patient on the controller implant site in the patient's body. This design provides for the patient to have limited but convenient control over the device operation, to the extent that the physician determines is appropriate.

Method of Treating Epilepsy

VNS and DBS. At least one stimulator (e.g., electrode 36, catheter 62) is implanted in contact with, or in proximity to, one or more sites on the vagus nerve and/or a volume of neural tissue (FIGS. 1 and 2). Stimulators may be coupled to the vagus nerve at any point along its length or on one of the nerve branches. For instance, stimulators may be placed bilaterally, e.g. both left and right vagus nerves. Similarly, at least one sensor (e.g., sensing electrode) is implanted in contact with, or in proximity to, a vagus nerve site and/or a volume of neural tissue. Depending upon the desired mode of treatment to be administered, a procedure for treating epilepsy may include implanting a selected type of stimulator/sensor device (e.g., stimulating and/or sensing electrode and/or plurality of electrodes, chemical catheter, sensor) in contact with neural tissue in the brain. Alternatively, or additionally, the surgical procedure may include implanting a device (stimulating and/or sensing electrode and/or plurality of electrodes, and/or chemical catheter, sensor) in contact with tissue in the patient's viscera, organs or peripheral nervous system.

FIG. 1 illustrates a preferred location of implanted controller 10 in the patient's chest in a cavity formed by the implanting surgeon just below the skin, much as a pacemaker pulse generator would be implanted. A representative treatment regimen to treat a particular epilepsy syndrome generally includes obtaining an above-described neurostimulation system that is configured and programmed or programmable to modulate neuronal activity of a predetermined area of neural tissue associated with that epilepsy syndrome.

At least one stimulator 36 (e.g., electrode, catheter outlet) is surgically implanted in the brain of a patient in need of treatment for epilepsy. Employing appropriate surgical techniques as are known in the art, a small opening is made in the skull and the stimulator is placed in, or proximal to, an area of the brain that comprises a "node" in the neural circuitry which is correlated with symptoms of the patient's epilepsy syndrome. For example, the target area may be associated with speech or with vision.

The present description focuses on one hemisphere of the brain. It should be understood, however, that stimulation and/or sensing of like structures on either or both sides of the brain is also contemplated. Accordingly, stimulation and/or sensing may be applied to sites in one or both hemispheres and may be carried out in at the same time or at different times, and may comprise the same or different stimuli. Areas of the brain that are of interest as stimulation sites include, but are not limited to, insula, subcallosal area, cingulate, thalamus, prefrontal cerebral cortex, mesial temporal lobe, cerebellum, hypothalamus, hippocampus, amygdala, brain stem and white matter tracts leading to an aforementioned area. Within the cingulate, the cingulate gyrus comprising the anterior cingulate or the posterior cingulate are especially preferred areas. Within the cortex, especially preferred areas include the motor cortex, prefrontal cortex, orbitofrontal cortex, premotor cortex, somatosensory cortex, cingulate cortex, anterior cingulate cortex, insular cortical region and Brodmann areas 8, 9, 10, 11. In the thalamus, the more preferred areas are the ventral medial thalamic nucleus, ventral posterior medial thalamic nucleus, parafascicular nucleus, subthalamic nucleus, dorsomedial thalamic nucleus, intralaminar thalamic nuclei, midline thalamic nuclei, anterior thalamus, anterior thalamic nuclei, nucleus reticularis thalami, and centromedian nucleus of the thalamus. Especially preferred areas of the hypothalamus are lateral hypothalamus, paraventricular nucleus of the hypothalamus, the bed nucleus of the stria terminalis, mamillary bodies, supraoptic nucleus, dorsomedial nucleus of the hypothalamus, lateral nucleus of the hypothalamus, tuberal nucleus of the hypothalamus. Areas of the brainstem/medulla that are especially preferred stimulation and/or sensing sites are locus ceruleus, dorsal raphe nucleus, nucleus of the solitary tract, the entirety of the solitary tract, the caudal ventrolateral medulla, and rostral ventrolateral medulla and parabrachial nucleus. Other regions of interest for stimulation and/or sensing are occipital lobe, temporal lobe, frontal lobe, parietal lobe, Wernicke's area, area tempestas, basal ganglia, globus pallidus, superior colliculus, striatum, ventral striatum, ventral pallidum, caudate nucleus, putamen, nucleus accumbens, substantia nigra, ventral tegmentum. Still other suitable areas for stimulation and/or sensing are Brodmann areas 24, 25, 32, piriform cortex, ventricular region, ventral pallidum, and forebrain circumventricular organs, reticulate substantia innominata, rostral midbrain, red nucleus, periaqueductal gray, and white matter tracts leading to or from an aforementioned area or nucleus.

In electrical stimulation mode, the implanted electrode is coupled to the signal generator of controller 10. As schematically shown in FIG. 3, for chemical/drug stimulation mode, a catheter connects the target tissue to a chemical/pharmaceutical delivery assembly (pump) that communicates with the controller 10. Leads 37, 39 are preferably routed under the scalp to an implanted controller 10, however they could also be routed externally to an implanted or external controller. A catheter may also be similarly routed to an implanted or externally located pump. A catheter that also includes at least one electrode may also be employed, if desired.

A treatment regimen may employ a system which includes a sensing capability that is operated to detect electrical or chemical activity in a selected area of the brain or volume of neural tissue. Feedback of the detected neuronal activity is provided to the controller so that the stimulation signal (e.g., one or more parameters such as pulse current, pulse width, frequency, and on-time or off-time) is automatically adjusted, thereby enhancing treatment of epilepsy. Particular areas of the brain suitable for sensing are mentioned above. More preferred areas for sensing neuronal activity are areas within the fronto-basal ganglionic-thalamocortical system, cortico-striato-thalamic system, mesolimbic pathway, mesocortical pathway, circuit of Papez and nigrostriatal pathway. Preferably the sensing of an above-mentioned brain area is obtained epidurally, subdurally, or on the patient's scalp. Alternatively, at least one sensing electrode 26, or other sensing device, is placed in contact with, or in proximity to, one or more site on the vagus nerve 27. FIG. 1 illustrates placement of a sensor on the patient's left vagus in the neck. The vagus nerve may be contacted at any point along its length or one of its branches. For instance, stimulating or sensing electrodes may be located directly on, or proximal to, the left and/or right vagus nerve(s) in a near-diaphragmatic location (e.g., supra-diaphragmatic or sub-diaphragmatic).

After sufficient healing from the surgical implantation procedure has taken place the physician selects appropriate stimulation signals by actuating neurostimulation system 1 to generate electrical stimuli in the form of electrical impulses according to a programmed regimen for deep brain stimulation of the selected area of the patient's brain. During the electrode implantation procedure, the physician checks the voltage and/or current level of the pulsed signal to ascertain that the voltage/current is adjusted to a magnitude at least slightly below a threshold of the patient at which adverse effects would occur. Typically, the stimulation level is programmed such that the patient does not experience significant adverse effects attributable to the DBS therapy, although variations in device parameters settings may be observed from patient to patient. In any event, the maximum amplitude of the voltage/current should be adjusted accordingly until a beneficial effect (e.g., alleviation of a generalized tonic-clonic seizure), with a suitable safety margin. The adverse effects and/or beneficial effects thresholds may change noticeably with time over a course of days after implantation, so the levels are preferably checked again in the first few days after implantation to determine whether any adjustment is necessary to maintain an effective regimen. The DBS regimen preferably employs an intermittent pattern of a period in which a repeating series of pulses is generated for stimulating the selected neural tissue in the brain, followed by a period in which no pulses are generated. The on/off duty cycle of these alternating periods of stimulation and no stimulation preferably has a ratio in which the off time is approximately 1.8 times the length of the on time. Preferably also, the width of each pulse is set to a value not greater than about 500 microseconds, and the pulse repetition frequency is programmed to be in a range of about 130 Hz. The above-described electrical and timing parameters of the stimulating signal used for DBS are merely exemplary and do not constitute a limitation of the scope of the present invention.

Figure 4:
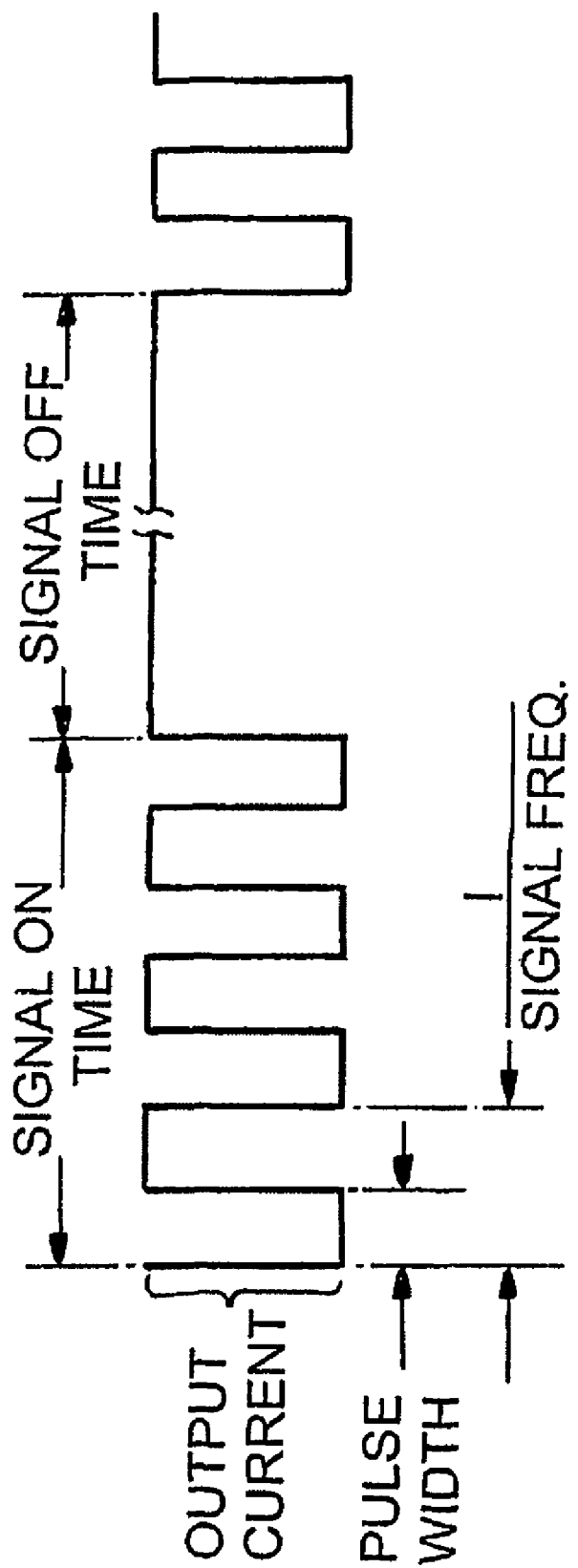
FIG. 4 is an illustrative idealized electrical output signal waveform of the signal generator useful for clarifying relevant parameters of the signal developed by the signal generator for application to the nerve, according to certain embodiments of the present invention.

Initial Setup of the System. As an aid to adjusting the programming of the system and optimizing the stimulating signal parameters for a particular patient's therapeutic regimen, a program of vagus nerve stimulation with selective deep brain sensing may be employed. This method includes placing an electrode in contact with, or in proximity to, one or more sites on the vagus nerve (preferably, the left vagus nerve in the neck of the patient), and contacting a sensing electrode with a selected afore-mentioned area of the patient's brain or a white matter tract leading from a selected area. Both electrodes are in communication with a controller/stimulus generator/processor unit, as described above. A predetermined electrical signal is applied to the vagus nerve electrode, causing modulation (e.g., stimulation or inhibition) of the electrical activity of the neural tissue that receives an electrical stimulus from the vagus nerve. An illustrative idealized electrical output signal waveform of the signal generator useful for clarifying relevant parameters of the signal developed by the signal generator for application to the nerve is shown in FIG. 4. The programming and settings of the controller/processor are adjusted to provide timing of bursts of electrical stimulation to the nerve, causing selective stimulation of at least one site on the vagus nerve, whereby one or more of the gustatory pathways, olfactory pathways, pro-inflammatory or anti-inflammatory pathways, respiratory pathways, cardiac pathways, baroreceptor pathways, and the somatosensory pathways are beneficially activated, causing a responsive attenuation of neural activity in various areas of the brain. Vagus nerve stimulation may also affect neurotransmitter pathways such as noradrenergic, serotoninergic, dopaminergic catecholaminergic, GABAergic, opioidergic and cholinergic pathways similarly. Neural activating circuits may include the circuit of Papez, mesolimbic pathway the mesocortical pathway or the nigrostriatal pathway. The effect of such responsive effect on the brain tissue may be excitatory or inhibitory and may potentiate acute and/or long-term changes in neuronal activity. The responsive modulation or change in electrical activity of the neuronal tissue in the area of the patient's brain contacted by the implanted electrode is sensed and communicated to the controller 10.

Alternatively, programming of the system and optimizing of the stimulating signal parameters for the patient's therapeutic regimen includes executing a program of selective DBS with selective deep brain sensing. For instance, a sensor is implanted in communication with a subcallosal area, and the system is then operated to sense electrical or chemical activity in the selected subcallosal area providing feedback to the controller to optimally adjust the stimulation for treating the patient's epilepsy. The stimulatory and sensed data is analyzed in the processor to determine any change in electrical activity of the selected brain area caused by application of a particular electrical signal. In this way, the signal parameters are adjusted under the supervision of the physician causing a responsive modulation of neural activity in selective areas of the brain. Such modulation of electrical activity of the selected area of the brain is correlated by the processor with observed or expected alleviation of a symptom of the patient's epilepsy.

Commencement of Therapy. The patient's epilepsy symptoms should be allowed to stabilize at approximately the preoperative level before the DBS regimen is actually administered. Treatment applied in the form of chronic intermittent electrical stimulation over each twenty-four hour period may be observed initially to result in no change in epilepsy symptoms in the patient. But after a period of several days of this DBS regimen, a discernible improvement in symptoms of the epilepsy will occur. For instance, in the case of generalized tonic-clonic epilepsy syndrome, stimulation of the centromedian thalamus is expected to attenuate the severity of seizures and/or to deter the onset of a seizure. The DBS treatment is not expected to adversely affect normal behavior in other aspects of the patient's life. A complete suspension of the DBS regimen would be expected to result in a relatively rapid return to the previous pattern and/or severity of epileptic events, ending after resumption of the DBS regimen. It is proposed that DBS stimulation of certain areas of the brain of individuals suffering from epilepsy may be a viable option for more effectively treating the condition than is presently possible with conventional therapies.

The following suggested therapeutic applications for the above-described system are illustrative, and are not meant to be limiting of the many possible combinations of stimulation and/or sensing modes that can be employed:

Selective Stimulation of Thalamus. In one treatment regimen, a predetermined stimulatory signal (e.g., electrical signal) is applied to a thalamus area in the patient's brain, and such stimulation of the selected thalamus area produces modulation of neuronal activity in a intralaminar thalamic nuclei. In another treatment regimen, by application of another predetermined stimulatory signal, stimulation of the selected thalamus area results in modulation of neuronal activity in one or more of the areas of the centromedian fascicular complex. As a result of such neuronal modulation of the thalamus, one or more symptoms of the patient's epilepsy syndrome, or the frequency of repeated occurrences of epileptic events is diminished.

An alternative treatment regimen is configured to apply a predetermined stimulatory signal (e.g., electrical, chemical/ pharmaceutical, magnetic) to a region of the thalamus causing modulation of the parafascicular nucleus, centromedian fascicular complex, ventral medial Vim thalamic nucleus, parafascicular complex, or another portion of the thalamus, the entirety of the thalamus, subthalamic nucleus (STN) or hypothalamus, to attenuate or decrease the frequency of repeated occurrences of epileptic events, such as epilepsy with generalized tonic-clonic seizures in childhood, in which the centromedian thalamus and anterior thalamus are commonly involved.

Selective Electrical Stimulation of Frontal Lobe. One therapeutic application of the above-described system is for treating a patient suffering from frontal lobe epilepsy, in which the individual's brain frontal lobe acts as a center or focal point for seizure onset. In this instance, the treatment regimen comprises surgically implanting in the brain of a patient a stimulation lead having a proximal end and a stimulation portion, wherein after implantation the stimulation portion is in communication with the focal point or an adjacent portion of the frontal lobe. The proximal end of the lead is coupled to a signal generator, which generates a predetermined electrical stimulation signal such that the signal electrically stimulates the selected neural tissue thereby modulating the neuronal activity of the affected tissue to attenuate or deter the onset of an epileptic event.

Selective Chemical Stimulation of Occipital Lobe. A patient may be suffering from benign occipital epilepsy with occipital paroxysms, or from benign occipital epilepsy with centrotemporal spikes. A suitable treatment regimen includes applying a predetermined stimulatory signal (e.g., electrical signal) to a portion of the occipital lobe of the person's brain, and such stimulation of the selected area modulates neuronal activity in the same or a different area of the brain. As a result of such neuronal modulation, one or more symptom of the patient's occipital lobe epilepsy syndrome is attenuated, and/ or the frequency of repeated occurrences of seizures is diminished.

In chemical/pharmaceutical stimulation mode, the physician surgically implants a catheter having a proximal end in fluid communication with a pump and a discharge portion for infusing a dosage of a chemical or drug, such that after implantation the discharge portion of the catheter is in communication with a selected brain area. Application of the predetermined stimulation signal comprises operating the pump to discharge the chemical/drug through the discharge portion of the catheter into the selected area, thereby treating the patient's epilepsy syndrome. Targeted neural tissue and the affected (modulated) neural tissue may be the same or different, depending on the selected chemical/pharmaceutical stimulation signal, similar to the above-described electrical stimulation mode. For instance, the protocol may include surgically implanting a catheter having a proximal end in fluid communication with a pump and a discharge portion for infusing a dosage of a pharmaceutical, wherein after implantation the discharge portion of the catheter is in communication with the occipital lobe of the patient's brain. The predetermined stimulation signal is applied by operating the pump to discharge the pharmaceutical through the discharge portion of the catheter into the occipital lobe, thereby modulating neural activity in that part of the brain to ameliorate symptoms of the disorder. Some applicable types of chemicals and/or pharmaceutical agents include inhibitory neurotransmitter agonists, excitatory neurotransmitter antagonists, agents that increases the level of an inhibitory neurotransmitter, agents that decrease the level of an excitatory neurotransmitter, and local anesthetic agents.

Selective Stimulation of Mesial Temporal Lobe. Another treatment regimen comprises surgically implanting an electrical stimulation lead having a proximal end and a stimulation portion so that, after implantation, the stimulation portion is in communication with a portion of the mesial temporal lobe of the patient's brain, eg. hippocampus or amygdala. The proximal end of the lead is coupled to a signal generator that generates a predetermined electrical stimulation signal whereby the signal electrically stimulates that area of the mesial temporal lobe to modulate the neuronal activity of the affected tissue which, in turn, ameliorates the patient's mesial temporal lobe epilepsy syndrome.

Selective Stimulation of Parietal Lobe. In still another treatment regimen a predetermined stimulatory signal (e.g., electrical signal) is applied to a portion of the parietal lobe of the person's brain, and such stimulation of the selected area modulates neuronal activity in the same or a different area of the brain. As a result of such neuronal modulation, one or more symptom of the patient's parietal lobe epilepsy syndrome is attenuated, and/or the frequency of repeated occurrences of seizures is diminished.

Selective Bimodal Stimulation—Electrical/Chemical DBS. A treatment regimen may include both electrical and chemical stimulation modes. The physician surgically implants an electrical stimulation lead having a proximal end and a stimulation portion, wherein after implantation the stimulation portion is in communication with an area of the person's brain (e.g., a region of the thalamus, comprising a focal point for onset of an epileptic event, or comprising a neural node associated with spreading of the seizure to other areas of the brain. The physician also surgically implants a catheter having a proximal end in fluid communication with a pump and a discharge portion for infusing a dosage of a chemical or a pharmaceutical agent, such that after implantation the discharge portion of the catheter is in communication with the selected area. The proximal end of the lead is coupled to a signal generator, and a predetermined electrical signal is generated by the signal generator such that the selected area is stimulated. Additionally, the pump is operated to discharge the chemical or pharmaceutical agent through the discharge portion of the catheter into the same or a different area of the brain, causing that area to be additionally stimulated by the chemical or pharmaceutical agent, to enhance attenuation or prevention of a seizure. Electrical and chemical stimulation may be applied simultaneously or sequentially, as determined by the physician.

Selective DBS with Feedback Sensing. When a sensing capability is also included in the system, the implantable or external processor is additionally configured for measuring, sensing, recording, monitoring the physiological activity, physiological event, physiological threshold, body or brain state. This is accomplished, for instance, by sensing electrical activity in the nerve (action potentials), in or from the brain, heart, gastro-intestinal tract, pancreas or other organs innervated by the vagus nerve, via an implanted electrode. Sensing can also include respiratory responses or pulmonary function, including carbon dioxide and oxygen levels. External monitoring can be performed by functional transcranial Doppler, FMRI scanner, PET scanner, FDG-PET, MEG or by conventional scalp EEG. Sensing of the heart can be monitored using HRV, RSA, heart rate, heart rhythm, blood pressure and/or baroreceptor activity. Preferably the sensed parameter is correlatable to the imminent onset of an epileptic episode. The processor and controller are configured such that the treatment parameters can be varied or adjusted based on adaptive learning, whereby the system detects activity or physiologic changes after stimulation and automatically adjusts the controller to attempt to deliver optimized therapy. The controller/processor can also determine the result of adverse stimulation and adjust the stimulation to prevent an adverse patient response.

Feedback or sensing is especially useful in an adaptive brain stimulation system. This system is employed for treating a patient suffering from epilepsy by stimulating a first brain region or a first set of brain regions in the patient according to a defined set of stimulation parameters which are derived according to a procedure that includes sensing a present state of the patient, and then comparing the resulting data related to the sensed present state of the patient to data related to a reference state, and obtaining comparison results. From those results, it is determined whether to make a change in the stimulation parameters, and if so, what change is to be made, depending on the comparison results. The attending physician then makes the appropriate changes in the stimulation parameters, as determined by the aforementioned comparison of present and reference states. The sensing, comparing, determining and adjusting steps are repeated any number of times, as deemed necessary. Stimulation of a different neural tissue (e.g., a second brain region or a second set of brain regions of the patient may also be carried out), depending on the comparison results. Preferably, stimulation of the vagus nerve causes modulation of a second brain region or set of brain regions, which produces a positive reinforcement (e.g., a decrease in severity or occurrence of epileptic events). The step of sensing a present state of the patient may comprise sensing a state of one or more peripheral regions of the patient's body. The changes that are made to the stimulation signal may comprise adjusting parameters so as to selectively stimulate one or more sites on the vagus nerve to activate the gustatory pathways, olfactory pathways, pro-inflammatory or anti-inflammatory pathways, respiratory pathways, cardiac pathways, baroreceptor pathways and the somatosensory pathways. Vagus nerve stimulation may also affect neurotransmitter pathways such as noradrenergic, serotoninergic, dopaminergic catecholaminergic, GABAergic, opioidergic and cholinergic pathways similarly.

Vagus Nerve Stimulation with Selective Deep Brain Sensing. In a variation of the foregoing bimodal stimulation method, vagus nerve stimulation is employed instead of, or in addition to, deep brain stimulation (DBS). In this variation of the method, one or more area of the vagus nerve is electrically stimulated instead of, or in addition to, electrically stimulating an area of the brain associated with the patient's epilepsy syndrome. At least one stimulation electrode or chemical/drug stimulation assembly is placed in contact with, or in proximity to, one or more area on the vagus nerve. The vagus nerve may be contacted at any point along its length or one of its branches. For instance, as illustrated in FIG. 1, electrode 26 is preferably a bipolar stimulating electrode, preferably of the helical type described in U.S. Pat. No. 4,573,481 (Bullara). The electrode assembly is surgically implanted on the vagus nerve 27 in the patient's neck. Alternatively, the physician may surgically implant a pair of stimulation electrodes on the left and right vagus nerve and the stimulation signal parameters are adjusted to bilaterally stimulate both vagus nerves, in synchrony or asynchronously, in order to selectively inhibit, excite, or block selective areas of the brain to alleviate symptoms of an epilepsy syndrome. The controller/processor is adjusted to provide timing of bursts of electrical bilateral stimulation to attenuate the neural activity in selective areas of the brain to achieve the desired result. The signal parameters may be adjusted so as to stimulate one or more site on the vagus nerve, whereby one or more of the gustatory pathways, olfactory pathways, pro-inflammatory or anti-inflammatory pathways, respiratory pathways, cardiac pathways, baroreceptor pathways, and the somatosensory pathways are beneficially activated. Similarly, vagus nerve stimulation may affect neurotransmitter pathways such as noradrenergic, serotoninergic, dopaminergic catecholaminergic, GABAergic, opioidergic and cholinergic pathways.

A vagus nerve stimulation configuration is especially useful for optimizing the stimulating signal parameters, as mentioned above. For instance, as illustrated in FIG. 1, an electrode 26 is coupled to a site on the vagus nerve of the individual, and communicates with controller 10 via lead 22. Another electrode 38, a sensing electrode or "sensor," is coupled to a selected area of the patient's brain, as indicated above, or a white matter tract leading from an aforementioned area or from a Brodmann area or nucleus therein. Electrode 38 is also in communication with a controller/stimulus generator/processor unit. A predetermined electrical signal is applied to the vagus nerve electrode, causing stimulation or inhibition (modulation) of the electrical activity of the neural tissue that receives an electrical stimulus from that the vagus nerve. The responsive modulation or change in electrical activity of the neuronal tissue is sensed by the implanted electrode and communicated to the controller/processor 10. The data is analyzed in the processor to determine whether application of a particular electrical signal causes a change in electrical activity of the selected brain area. Such modulation of electrical activity of the selected area is also correlated by the processor with subjective or objective data indicating attenuation or deterrence of a symptom of the patient's epilepsy syndrome.

Combined DBS and VNS. One procedure in which deep brain stimulation (DBS) and vagus nerve stimulation (VNS) are employed together includes coupling a first electrode to the vagus nerve of the patient. FIG. 1 illustrates an electrode coupled to a patient's left vagus nerve in the neck. A second electrode is coupled to a selected area of the patient's brain that is known or expected to be associated with a particular epilepsy syndrome (e.g., intralaminar nuclei and/or nucleus reticularis, in the case of epilepsy syndromes characterized by absence seizures or complex partial seizures). A predetermined therapeutic electrical signal is applied to the first electrode, to stimulate the vagus nerve, and a second predetermined therapeutic electrical signal is applied to the second electrode to stimulate the neural tissue. As a result of the dual application of the first and second signals, advantageous modulation of the neuronal activity of the selected area of neural tissue is obtained which attenuates or deters onset of an epilepsy symptom. In an alternative treatment configuration, the stimulation parameters may be adjusted to bilaterally stimulate both vagus nerves, for instance, in synchrony or asynchronously, in order to selectively inhibit, excite, or block selective areas of the brain to provide the desired alleviation of symptoms of an epilepsy syndrome. The controller may be adjusted to provide timing of bursts of bilateral electrical stimulation to cause attenuation of neural activity in selective areas of the brain.

Combined DBS/VNS—Bimodal Electrical/Chemical Stimulation. Another representative combined DBS/VNS treatment includes surgically implanting an electrode and lead assembly having a proximal end and a stimulation portion, wherein after implantation the stimulation portion (i.e., electrode) is in communication with either a site on the vagus nerve or an above-mentioned brain area involved with the patient's epilepsy syndrome. The physician also surgically implants a catheter having a proximal end in fluid communication with a pump and a discharge portion for infusing a dosage of a chemical agent. After implantation the discharge portion of the catheter is in communication with a subcallosal area. The physician couples the proximal end of the lead to a signal generator. An appropriate electrical signal is created using the signal generator and is applied via the electrode and lead assembly, causing the signal to electrically stimulate the selected brain area. In concert with the electrical stimulation of the selected brain area or selected area of a vagus nerve, the pump operates to discharge the chemical agent through the discharge portion of the catheter into the same or a different brain area (which is also involved with the epilepsy syndrome), to provide a combined, bi-modal therapeutic treatment for epilepsy, preferably optimized for treating a particular epilepsy syndrome.

Triggered activation/deactivation. Preferably the desired stimulation, and resulting modulation, can be triggered by sensing of a predetermined event or condition or by manual activation from an external device, or from physician input or from patient input. If an above-described manual activation switch is included on the implantable controller, and should the physician determine that it is appropriate for the patient to have limited control over the device, the programming of the processor is adjusted to allow the signal generator to emit a predetermined stimulation signal upon detection by the controller of the requisite manual input from the patient.

Magnetic stimulation. As an alternative to surgical implantation of a DBS stimulator, an area of the brain such as the orbitofrontal cortex may instead be stimulated via transcranial magnetic stimulation. Thus, the stimulus can be electrical, chemical/drug, or magnetic, or a combination of any of those modes.

Combined Stimulation and Drug Therapies for Treating Epilepsy. An above-described stimulation regimen may be combined with a conventional drug therapy, if deemed appropriate by the physician. For instance, a conventional anti-epilepsy drug could be administered to the patient during the course of DBS treatment for epilepsy. Some pharmaceutical agents conventionally used for treatment of epilepsy include Carbamazepine, Tegretol, Ethosuximide (Emeside™), Zarontin, Lamotrigine (Lamictal™), Oxcarbazepine (Trileptal™), Sodium valproate, Epilim, Acetazolamide (Diamox™), Clobazam (Frisium™), Clonazepam (Rivotril™), Gabapentin (Neurontin™), Levetiracetam (Keppra™), Phenobarbitone, Phenytoin, Epanutin, Piracetam (Nootropil™), Pregabalin (Lyrica™), Primidone (Mysoline™), Tiagabine (Gabitril™), Topiramate (Topama™) and Vigabatrin (Sabril™). Additionally, or alternatively, one or more of these drugs may be dispensed at an above-mentioned location in the brain via an implantable drug delivery device, if desired.

Treatment of Other Neurological Disorders.

Neurological disorders, including motor disorders, are also treated in a manner similar to an above-described method for treating epilepsy, to obtain at least some measure of relief from the symptoms or occurrence of the motor disorder. Treatable motor disorders include, but are not limited to, tremor and the class of tremor disorders, intentional tremor, dystonia, tardive-diskenesia, ballism, spasticity, athetosis, rigidity, akinesia, bradykinesia, or other hyperkinetic or hypokinetic disorder, coma and paralysis. A representative treatment may include the steps of: (a) surgically implanting an electrical stimulation lead having a proximal end and a stimulation portion, wherein after implantation the stimulation portion is in communication with a region of the thalamus; (b) coupling the proximal end of the lead to a signal generator; and (c) generating an electrical signal with the signal generator wherein said signal electrically stimulates the region of the thalamus thereby treating the epilepsy or other neurological disorder, or other disorder. The method may further comprise the steps of: (d) surgically implanting a catheter having a proximal end coupled to a pump and a discharge portion for infusing a dosage of a pharmaceutical, wherein after implantation the discharge portion of the catheter is in communication with the region of the thalamus; and (e) operating the pump to discharge the pharmaceutical through the discharge portion of the catheter into the region of the thalamus thereby treating the neurological disorder. The pharmaceutical may comprise an inhibitory neurotransmitter agonist, an excitatory neurotransmitter antagonist, an agent that increases the level of an inhibitory neurotransmitter, an agent that decrease the level of an excitatory neurotransmitter, or a local anesthetic agent, for instance. Other treatment modalities discussed above with respect to epilepsy treatment are expected to be similarly applicable to treating motor disorders. All of the above-described methods are believed to be useful to physicians in formulating appropriate therapeutic treatment of patients who suffer from epilepsy or another neurological disorder.

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. For instance, it should be understood that the various stimulation, sensing and activation modes, programmable features, and the like, that are described herein may be rearranged or employed in different combinations than those expressly exemplified. Many variations and modifications of the embodiments disclosed herein are possible and are within the scope of the invention. Accordingly, the scope of protection is not limited by the description set out above, but is only limited by the claims which follow, that scope including all equivalents of the subject matter of the claims. The disclosures of all patents, patent applications and publications cited herein are hereby incorporated herein by reference, to the extent that they provide exemplary, procedural or other details supplementary to those set forth herein.

What is claimed is:

1. A method of treating an individual suffering from epilepsy, the method comprising:
    applying a first stimulation signal to a first stimulator configured to be coupled to a stimulation site comprising a volume of neural tissue in an area of the individual's brain selected from the group consisting of insula, subcallosal area, cingulate, thalamus, prefrontal cerebral cortex, mesial temporal lobe, cerebellum, hypothalamus, hippocampus, amygdala, brain stem, occipital lobe, temporal lobe, frontal lobe, parietal lobe, Wernicke's area, area tempestas, basal ganglia, globus pallidus, superior colliculus, striatum, ventral striatum, ventral pallidum, caudate nucleus, putamen, nucleus accumbens, substantia nigra, ventral tegmentum, Brodmann areas 24, 25, 32, piriform cortex, ventricular region, ventral pallidum, and forebrain circumventricular organs, reticulate substantia innominata, rostral midbrain, red nucleus, periaqueductal gray, and white matter tracts leading to an aforementioned area or nucleus, wherein the first stimulation signal causes modulation of the neuronal activity of neural tissue in said selected area of the brain;
    applying a second stimulation signal to a second stimulator configured to be coupled to a site on the vagus nerve of the individual such that said second stimulation signal causes modulation of the neuronal activity in said vagus nerve, wherein said first and/or second stimulation signal causes modulation of neuronal activity in at least one brain area of said individual different than said area coupled to said first stimulator, and wherein said combination of modulations attenuate at least one epilepsy symptom and/or deter recurrence of an epileptic event;
    after applying the first stimulation signal to the selected area of the brain, sensing neuronal activity in the selected area of the brain with at least one first sensor;
    after applying the second stimulation signal to the vagus nerve, sensing neuronal activity in the different area of the brain with at least one second sensor; and
    based on data collected from the sensing in at least the different area of the brain, adapting a stimulation parameter of the first and/or second stimulation signal to increase the attenuation of at least one epilepsy symptom and/or the deterrence of an epileptic event for a subsequent combination of modulations.

2. The method of claim 1 wherein said second stimulation signal causes stimulation of a site on the vagus nerve, whereby at least one vagus nerve pathway or neural activating circuit is affected causing a responsive effect on neural activity in at least one area of the brain to further attenuate the same or different epilepsy symptom and/or to further deter recurrence of an epileptic event.

3. The method of claim 2 wherein said vagus nerve pathway or neural activating circuit is chosen from the group consisting of gustatory pathways, olfactory pathways, pro-inflammatory or anti-inflammatory pathways, respiratory pathways, cardiac pathways, baroreceptor pathways, somatosensory pathways, noradrenergic pathways, serotoninergic pathways, dopaminergic pathways, catecholaminergic pathways, GABAergic pathways, opioidergic pathways, cholinergic pathways, circuit of Papez, mesolimbic pathway, mesocortical pathway and nigrostriatal pathway.

4. The method of claim 3 wherein said responsive effect on said area of the brain is excitatory or inhibitory and potentiates acute and/or long-term changes in neuronal activity of said area of the brain.

5. The method of claim 1 wherein said first stimulation signal comprises a first acute stimulation component and a first chronic stimulation component and/or said second stimulation signal comprises a second acute stimulation component and a second chronic stimulation component.

6. The method of claim 5 wherein said first acute stimulation component comprises a higher intensity level of stimulation and shorter duration than said first chronic stimulation component and/or said second acute stimulation component comprises a higher intensity level of stimulation and shorter duration than said second chronic stimulation component.

7. The method of claim 5 wherein said first and/or second acute stimulation component comprises a duration in the range of one day to six months.

8. The method of claim 1 wherein said selected area of the individual's brain comprises a portion of the cingulate gyrus comprising the anterior cingulate or the posterior cingulate.

9. The method of claim 1 wherein said selected area of the individual's brain comprises a portion of the cortex chosen from the group consisting of motor cortex, prefrontal cortex, orbitofrontal cortex, premotor cortex, somatosensory cortex, cingulate cortex, anterior cingulate cortex, insular cortical region and Brodmann areas 8, 9, 10, 11.

10. The method of claim 1 wherein said selected area of the individual's brain comprises a portion of the thalamus chosen from the group consisting of ventral medial thalamic nucleus, ventral posterior medial thalamic nucleus, parafascicular nucleus, subthalamic nucleus, dorsomedial thalamic nucleus, intralaminar thalamic nuclei, midline thalamic nuclei, anterior thalamus, anterior thalamic nuclei, nucleus reticularis thalami, and centromedian nucleus of the thalamus.

11. The method of claim 1 wherein said selected area of the individual's brain comprises a portion of the hypothalamus chosen from the group consisting of lateral hypothalamus, paraventricular nucleus of the hypothalamus, the bed nucleus of the stria terminalis, mamillary bodies, supraoptic nucleus, dorsomedial nucleus of the hypothalamus, lateral nucleus of the hypothalamus, tuberal nucleus of the hypothalamus.

12. The method of claim 1 wherein said selected area of the individual's brain comprises a portion of the brainstem/medulla chosen from the group consisting of locus ceruleus, dorsal raphe nucleus, nucleus of the solitary tract, the entirety of the solitary tract, the caudal ventrolateral medulla, rostral ventrolateral medulla and parabrachial nucleus.

13. The method of claim 1 wherein said first stimulator is a first electrode and said second stimulator is a second electrode, and said method further comprises:
   providing at least one programmable electrical signal generator coupled to said first and second electrodes;
   programming said at least one electrical signal generator to define each of said first and second stimulation signals by a plurality of electrical parameters comprising a current magnitude, a pulse frequency, and a pulse width, wherein said parameters are selected to attenuate or deter the occurrence of at least one symptom of epilepsy.

14. The method of claim 1 wherein said first and/or second stimulator comprises at least one chemical dispensing assembly comprising a chemical filled reservoir and a catheter in communication with a pump, said catheter comprising a dispensing end located on or near said nerve or brain area, and said first and/or second stimulation signal each comprises a therapeutic pumping signal, said method comprising:
   operating at least one said pump such that said chemical contacts said selected brain area and/or vagus nerve, whereby the neuronal activity of the contacted brain area and/or nerve is modified, and such modification of neuronal activity causes attenuation or deterrence of at least one symptom of epilepsy.

15. The method of claim 14 wherein said chemical agent is selected from the group consisting of inhibitory neurotransmitter agonists, excitatory neurotransmitter antagonists, agents that increase the level of an inhibitory neurotransmitter, agents that decrease the level of an excitatory neurotransmitter, and local anesthetic agents.

16. The method of claim 1 wherein said selected area of the individual's brain comprises the thalamus or a white matter tract leading to a portion of the thalamus.

17. The method of claim 1 wherein the adapting of a stimulation parameter of the first and/or second stimulation signal comprises:
   a comparator comparing the sensed neuronal activity in the different area of the brain to a predetermined electrical state of the different area of the brain;
   determining from the comparison that the modulation of electrical activity in the different area of the brain was not sufficient to treat the individual's epilepsy adequately; and
   a controller coupled to the comparator determining a change in the stimulation parameter of the first and/or second stimulation signal to increase the attenuation of at least one epilepsy symptom and/or the deterrence of an epileptic event for a subsequent combination of modulations.

18. A method of treating an individual suffering from epilepsy, the method comprising:
   applying a first stimulation signal to a first stimulator configured to be coupled to a stimulation site comprising a volume of neural tissue in an area of the individual's brain selected from the group consisting of insula, subcallosal area, cingulate, thalamus, prefrontal cerebral cortex, mesial temporal lobe, cerebellum, hypothalamus, hippocampus, amygdala, brain stem, occipital lobe, temporal lobe, frontal lobe, parietal lobe, Wernicke's area, area tempestas, basal ganglia, globus pallidus, superior colliculus, striatum, ventral striatum, ventral pallidum, caudate nucleus, putamen, nucleus accumbens, substantia nigra, ventral tegmentum, Brodmann areas 24, 25, 32, piriform cortex, ventricular region, ventral pallidum, and forebrain circumventricular organs, reticulate substantia innominata, rostral midbrain, red nucleus, periaqueductal gray, and white matter tracts leading to an aforementioned area or nucleus, wherein the first stimulation signal causes modulation of the neuronal activity of neural tissue in said selected area of the brain;
   applying a second stimulation signal to a second stimulator configured to be coupled to a site on the vagus nerve of the individual such that said second stimulation signal causes modulation of the neuronal activity in said vagus nerve, wherein said first and/or second stimulation signal causes modulation of neuronal activity in at least one brain area of said individual different than said area coupled to said first stimulator, and wherein said combination of modulations attenuate at least one epilepsy symptom and/or deter recurrence of an epileptic event;
   after applying the second stimulation signal to the vagus nerve, sensing neuronal activity in the selected area of the brain or the different area of the brain with at least one sensor; and
   based on data collected from the sensing and using a controller coupled to the sensor and to the first or second stimulator, adapting a stimulation parameter of the first or second stimulation signal to increase the attenuation of at least one epilepsy symptom and/or the deterrence of an epileptic event for a subsequent combination of modulations.

19. A method of treating an individual suffering from epilepsy, the method comprising:
   applying a first stimulation signal to a first stimulator configured to be coupled to a stimulation site comprising a volume of neural tissue in an area of the individual's brain selected from the group consisting of insula, subcallosal area, cingulate, thalamus, prefrontal cerebral cortex, mesial temporal lobe, cerebellum, hypothalamus, hippocampus, amygdala, brain stem, occipital lobe, temporal lobe, frontal lobe, parietal lobe, Wernicke's area, area tempestas, basal ganglia, globus pallidus, superior colliculus, striatum, ventral striatum, ventral pallidum, caudate nucleus, putamen, nucleus accumbens, substantia nigra, ventral tegmentum, Brodmann areas 24, 25, 32, piriform cortex, ventricular region, ventral pallidum, and forebrain circumventricular organs, reticulate substantia innominata, rostral midbrain, red nucleus, periaqueductal gray, and white matter tracts leading to an aforementioned area or nucleus, wherein the first stimulation signal causes modulation of the neuronal activity of neural tissue in said selected area of the brain;
   applying a second stimulation signal to a second stimulator configured to be coupled to a site on the vagus nerve of the individual such that said second stimulation signal causes modulation of the neuronal activity in said vagus nerve, wherein said first and/or second stimulation signal causes modulation of neuronal activity in at least one brain area of said individual different than said area coupled to said first stimulator, and wherein said combination of modulations attenuate at least one epilepsy symptom and/or deter recurrence of an epileptic event;

after applying the first stimulation signal to the selected area of the brain and after applying the second stimulation signal to the vagus nerve, sensing neuronal activity in the selected area of the brain or the different area of the brain with at least one sensor; and based on data collected from the sensing, adapting a stimulation parameter of the first and/or second stimulation signal to increase the attenuation of at least one epilepsy symptom and/or the deterrence of an epileptic event for a subsequent combination of modulations.

20. The method of claim 19 wherein the adapting of a stimulation parameter of the first and/or second stimulation signal comprises:

a comparator comparing the sensed neuronal activity in the selected area of the brain or the different area of the brain to a predetermined electrical state of the respective selected area of the brain or different area of the brain;

determining from the comparison that the modulation of electrical activity in the selected area of the brain or the different area of the brain was not sufficient to treat the individual's epilepsy adequately; and a controller coupled to the comparator determining a change in the stimulation parameter of the first and/or second stimulation signal to increase the attenuation of at least one epilepsy symptom and/or the deterrence of an epileptic event for a subsequent combination of modulations.

* * * * *